US010117706B2

(12) United States Patent
Rupp

(10) Patent No.: US 10,117,706 B2
(45) Date of Patent: Nov. 6, 2018

(54) ELECTROSURGICAL INSTRUMENT WITH INTEGRAL TISSUE REMOVAL FEATURE

(71) Applicant: Ethicon Endo-Surgery, Inc., Cincinnati, OH (US)

(72) Inventor: Kip M. Rupp, New Richmond, OH (US)

(73) Assignee: Ethicon LLC, Guaynabo, PR (US)

( * ) Notice: Subject to any disclaimer, the term of this patent is extended or adjusted under 35 U.S.C. 154(b) by 382 days.

(21) Appl. No.: 14/577,183

(22) Filed: Dec. 19, 2014

(65) Prior Publication Data
US 2016/0175027 A1 Jun. 23, 2016

(51) Int. Cl.
| A61B 18/14 | (2006.01) |
| A61B 18/00 | (2006.01) |
| A61B 17/072 | (2006.01) |

(52) U.S. Cl.
CPC .............................. *A61B 18/1445* (2013.01); *A61B 2017/07285* (2013.01); *A61B 2018/0063* (2013.01); *A61B 2018/0091* (2013.01); *A61B 2018/00184* (2013.01); *A61B 2018/00601* (2013.01); *A61B 2018/00976* (2013.01); *A61B 2018/1455* (2013.01)

(58) Field of Classification Search
CPC ............ A61B 18/1442; A61B 18/1445; A61B 18/1447; A61B 2018/1452; A61B 2018/145; A61B 2018/1455; A61B 2018/1457; A61B 2018/146; A61B 2018/1462; A61B 17/32113; A61B 10/06; A61B 10/0275; A61B 10/0233
USPC .......................................................... 14/52
See application file for complete search history.

(56) References Cited

U.S. PATENT DOCUMENTS

| 4,307,720 A | * | 12/1981 | Weber, Jr. .......... A61B 18/1402 604/22 |
| 4,805,823 A | | 2/1989 | Rothfuss |
| 5,415,334 A | | 5/1995 | Williamson et al. |
| 5,465,895 A | | 11/1995 | Knodel et al. |
| 5,597,107 A | | 1/1997 | Knodel et al. |
| 5,632,432 A | | 5/1997 | Schulze et al. |
| 5,673,840 A | | 10/1997 | Schulze et al. |
| 5,704,534 A | | 1/1998 | Huitema et al. |
| 5,814,055 A | | 9/1998 | Knodel et al. |

(Continued)

OTHER PUBLICATIONS

U.S. Appl. No. 61/410,603, filed Nov. 5, 2010.
U.S. Appl. No. 61/550,768, filed Oct. 24, 2011.

*Primary Examiner* — Jaymi Della
*Assistant Examiner* — Tigist Demie
(74) *Attorney, Agent, or Firm* — Frost Brown Todd LLC

(57) ABSTRACT

An apparatus for operating on tissue includes an elongate shaft extending distally from a body and an end effector at a distal end of the elongate shaft. The end effector includes a first jaw that is selectively pivotable toward and away from a second jaw to capture tissue and a firing beam. The firing beam is configured to advance relative to the first and second jaws to sever captured tissue and retract relative to the first and second jaws after the captured tissue has been severed. The apparatus further includes a debris removal element in communication with the firing beam. The debris removal element is configured to engage at least a portion of the firing beam at least during retraction of the firing beam relative to the first and second jaws to thereby remove at least some debris from the firing beam.

19 Claims, 13 Drawing Sheets

(56) References Cited

U.S. PATENT DOCUMENTS

| | | | |
|---|---|---|---|
| 6,126,653 A * | 10/2000 | Hajjar | A61B 18/24 606/15 |
| 6,245,070 B1 * | 6/2001 | Marquis | A61B 18/1442 606/51 |
| 6,500,176 B1 | 12/2002 | Truckai et al. | |
| 6,783,524 B2 | 8/2004 | Anderson et al. | |
| 6,978,921 B2 | 12/2005 | Shelton et al. | |
| 7,000,818 B2 | 2/2006 | Shelton et al. | |
| 7,112,201 B2 | 9/2006 | Truckai et al. | |
| 7,125,409 B2 | 10/2006 | Truckai et al. | |
| 7,143,923 B2 | 12/2006 | Shelton et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,303,108 B2 | 12/2007 | Shelton | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,367,485 B2 | 5/2008 | Shelton et al. | |
| 7,380,695 B2 | 6/2008 | Doll et al. | |
| 7,380,696 B2 | 6/2008 | Shelton et al. | |
| 7,381,209 B2 | 6/2008 | Truckai et al. | |
| 7,404,508 B2 | 7/2008 | Smith et al. | |
| 7,343,715 B2 | 10/2008 | Ito et al. | |
| 7,721,930 B2 | 5/2010 | McKenna et al. | |
| 7,967,819 B2 * | 6/2011 | Suzuki | A61B 18/1445 606/48 |
| 8,408,439 B2 | 4/2013 | Huang et al. | |
| 8,453,914 B2 | 6/2013 | Laurent et al. | |
| 8,461,744 B2 | 6/2013 | Wiener et al. | |
| 8,477,595 B2 | 7/2013 | Schousterman et al. | |
| 8,888,809 B2 | 11/2014 | Davison et al. | |
| 8,939,974 B2 | 1/2015 | Boudreaux et al. | |
| 8,951,248 B2 | 2/2015 | Messerly et al. | |
| 8,956,349 B2 | 2/2015 | Aldridge et al. | |
| 8,986,302 B2 | 3/2015 | Aldridge et al. | |
| 9,039,695 B2 | 5/2015 | Giordano et al. | |
| 9,050,093 B2 | 6/2015 | Aldridge et al. | |
| 9,060,776 B2 | 6/2015 | Yates et al. | |
| 9,089,327 B2 | 7/2015 | Worrell et al. | |
| 9,089,360 B2 | 7/2015 | Messerly et al. | |
| 9,161,803 B2 | 10/2015 | Yates et al. | |
| 9,220,559 B2 | 12/2015 | Worrell et al. | |
| 9,402,682 B2 | 8/2016 | Worrell et al. | |
| 2003/0199870 A1 * | 10/2003 | Truckai | A61B 18/1442 606/51 |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2011/0160731 A1 * | 6/2011 | Bleich | A61B 17/29 606/79 |
| 2011/0290853 A1 * | 12/2011 | Shelton, IV | A61B 17/07207 227/177.1 |
| 2012/0078243 A1 | 3/2012 | Worrell et al. | |
| 2012/0078244 A1 * | 3/2012 | Worrell | A61B 17/07207 606/33 |
| 2013/0023868 A1 | 1/2013 | Worrell et al. | |

* cited by examiner

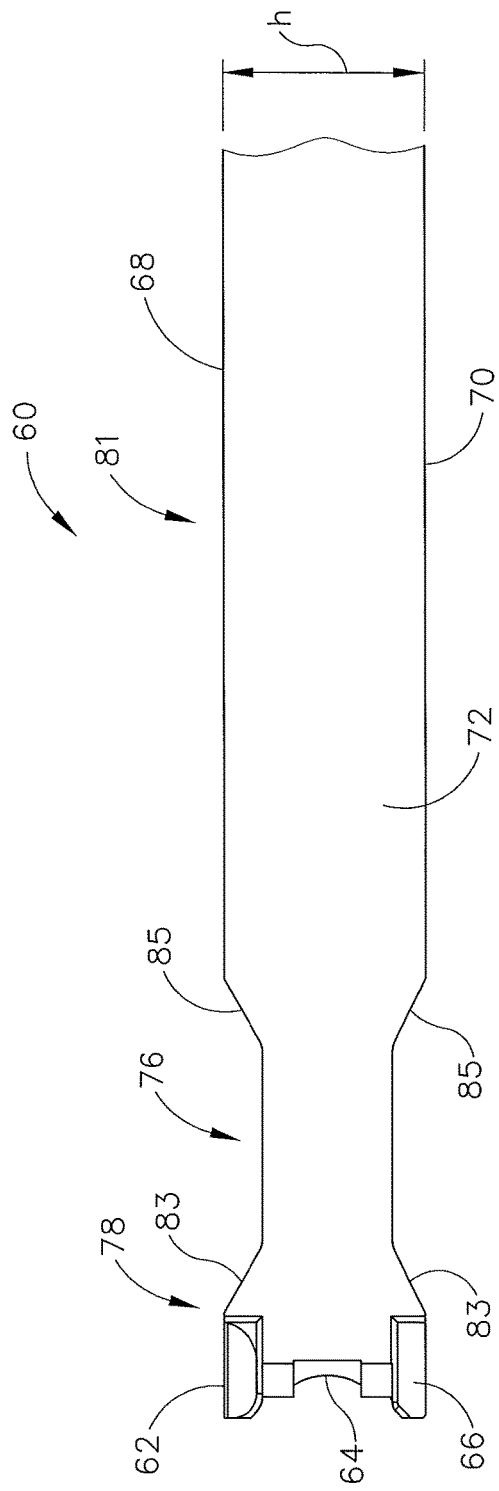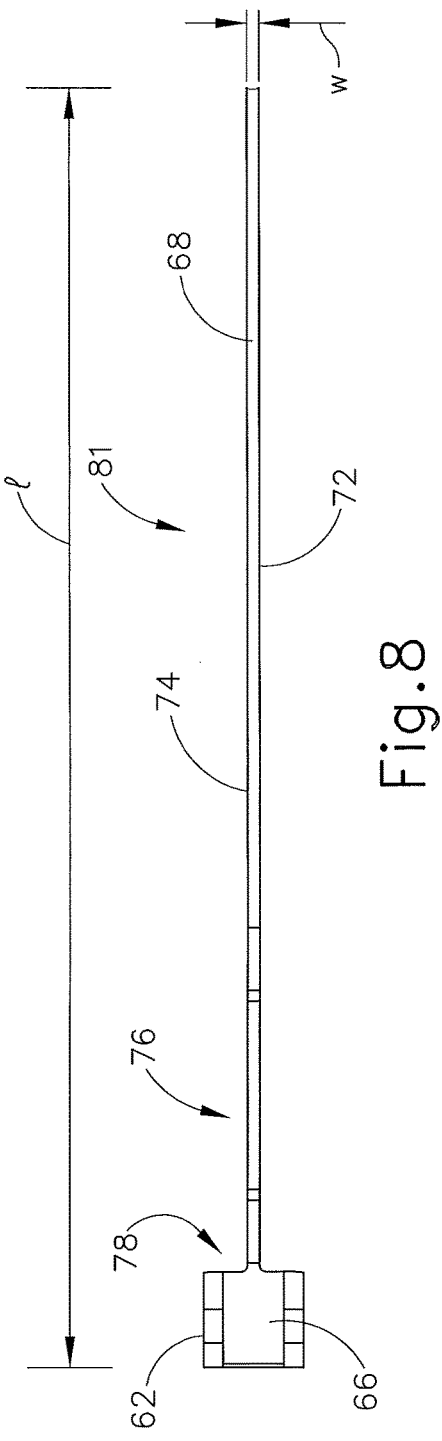

ELECTROSURGICAL INSTRUMENT WITH INTEGRAL TISSUE REMOVAL FEATURE

BACKGROUND

A variety of surgical instruments include a tissue cutting element and one or more elements that transmit radio frequency (RF) energy to tissue (e.g., to coagulate or seal the tissue). An example of such an electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, is now U.S. Pat. No. 8,939,974, issued Jan. 27, 2015, the disclosure of which is incorporated by reference herein; U.S. Pat. No. 8,888,809, entitled "Surgical Instrument with Jaw Member," issued Nov. 18, 2014, the disclosure of which is incorporated by reference herein; U.S. Pub. No. 2012/0116379, entitled "Motor Driven Electrosurgical Device with Mechanical and Electrical Feedback," published May 10, 2012, U.S. Pat. No. 9,161,803, issued Oct. 20, 2015, the disclosure of which is incorporated by reference herein; U.S. Pub. No. 2012/0078243, entitled "Control Features for Articulating Surgical Device," published Mar. 29, 2012, now U.S. Pat. No. 9,877,720, issued Jan. 30, 2018, the disclosure of which is incorporated by reference herein; U.S. Pub. No. 2012/0078247, entitled "Articulation Joint Features for Articulating Surgical Device," published Mar. 29, 2012, now U.S. Pat. No. 9,402,682, issued Aug. 2, 2016, the disclosure of which is incorporated by reference herein; U.S. Pub. No. 2013/0030428, entitled "Surgical Instrument with Multi-Phase Trigger Bias," published Jan. 31, 2013, now U.S. Pat. No. 9,089,327, issued Jul. 28, 2015, the disclosure of which is incorporated by reference herein; and U.S. Pub. No. 2013/0023868, entitled "Surgical Instrument with Contained Dual Helix Actuator Assembly," published Jan. 31, 2013, now U.S. Pat. No. 9,545,253, issued Jan. 17, 2017, the disclosure of which is incorporated by reference herein.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 7 depicts a partial side elevational view of the firing beam of FIG. 5;

FIG. 8 depicts a partial bottom plan view of the firing beam of FIG. 5;

Figure 1:
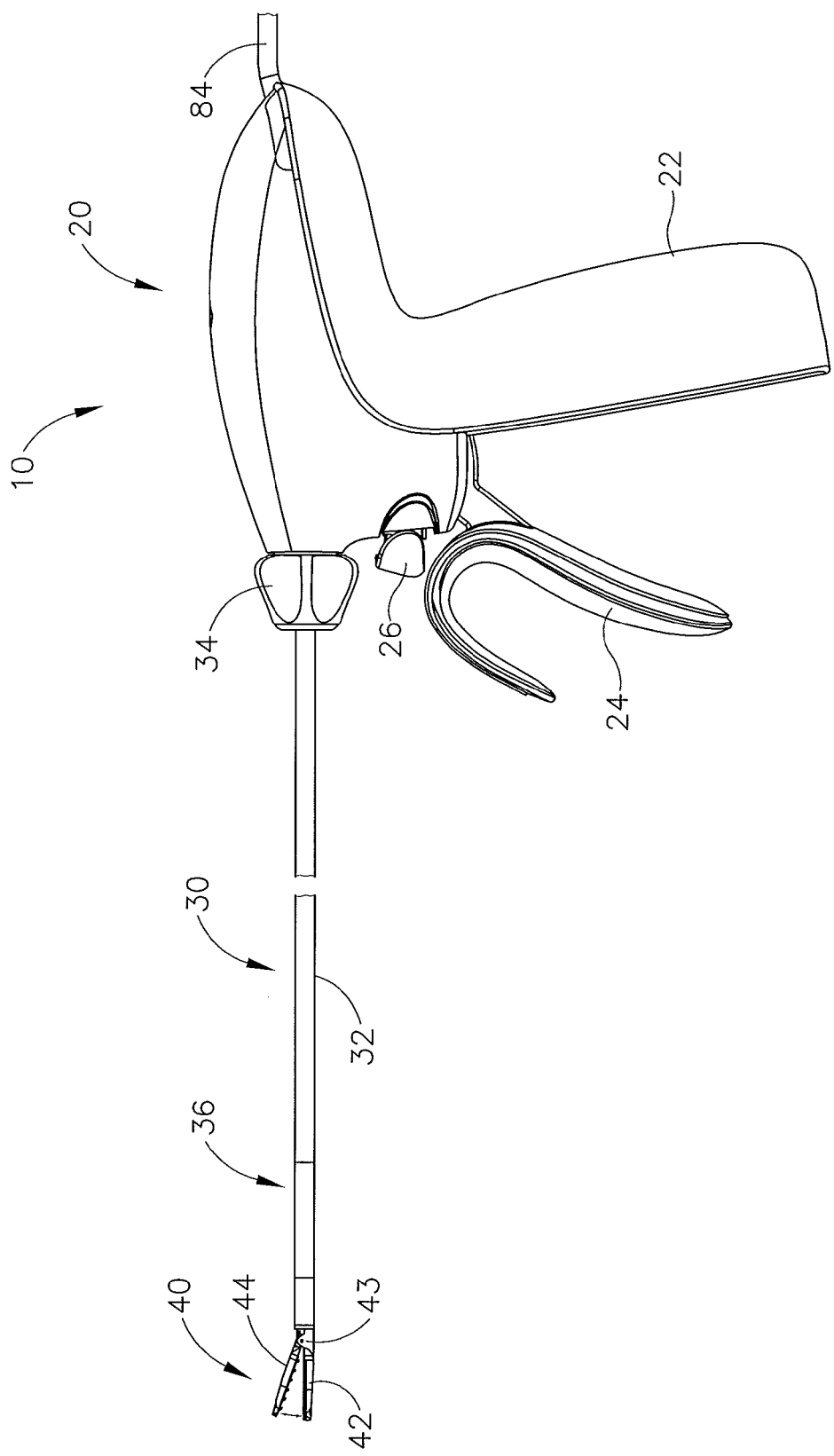
FIG. 1 depicts a side elevational view of an exemplary electrosurgical medical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Electrosurgical Device with Articulation Feature

FIGS. 1-4 show an exemplary electrosurgical instrument (10) that is constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pub. No. 2011/0087218, now U.S. Pat. No. 8,939,974, issued Jan. 27, 2015; U.S. Pub. No. 2012/0083783, now U.S. Pat. No. 8,888,809, issued Nov. 18, 2014; U.S. Pub. No. 2012/0116379, now U.S. Pat. No. 9,161,803, issued Oct. 20, 2015; U.S. Pub. No. 2012/0078243, now U.S. Pat. No. 9,877,720, issued Jan. 30, 2018; U.S. Pub. No. 2012/0078247, now U.S. Pat. No. 9,402,682, issued Aug. 2, 2016; U.S. Pub. No. 2013/0030428, now U.S. Pat. No. 9,089,327, issued Jul. 28, 2015; and/or U.S. Pub. No. 2013/0023868, now U.S. Pat. No. 9,545,253, issued Jan. 17, 2017. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), and an activation button (26). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. In addition or in the alternative, trigger (24) may serve as an electrical and/or mechanical lockout against button (26), such that button (26) cannot be effectively activated unless trigger (24) is being squeezed simultaneously. It should be understood that pistol grip (22), trigger (24), and button (26) may be modified, substituted, supplemented, etc. in any suitable way, and that the descriptions of such components herein are merely illustrative.

Shaft (30) of the present example includes a rigid outer sheath (32) and an articulation section (36). Articulation section (36) is operable to selectively laterally deflect end effector (40) at various angles relative to the longitudinal axis defined by sheath (32). In some versions, articulation section (36) and/or some other portion of outer sheath (32) includes a flexible outer sheath (e.g., a heat shrink tube, etc.) disposed about its exterior. Articulation section (36) of shaft (30) may take a variety of forms. By way of example only, articulation section (36) may be configured in accordance with one or more teachings of U.S. Pub. No. 2012/0078247, now U.S. Pat. No. 9,402,682, issued Aug. 2, 2016, the disclosure of which is incorporated by reference herein. As another merely illustrative example, articulation section (36) may be configured in accordance with one or more teachings of U.S. Pub. No. 2012/0078248, now U.S. Pat. No. 9,220,559, issued Dec. 29, 2015, entitled "Articulation Joint Features for Articulating Surgical Device," published Mar. 29, 2012, the disclosure of which is incorporated by reference herein. Various other suitable forms that articulation section (36) may take will be apparent to those of ordinary skill in the art in view of the teachings herein. It should also be understood that some versions of instrument (10) may simply lack articulation section (36).

In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating articulation section (36) or any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating articulation section (36) or any portion of shaft (30) that is proximal of articulation section (36). Other suitable rotation schemes will be apparent to those of ordinary skill in the art in view of the teachings herein. Of course, rotatable features may simply be omitted if desired.

Although not shown, it should be understood that in some examples instrument (10) may include an articulation control (not shown). In such examples, the articulation control may be operable to selectively control articulation section (36) of shaft (30), to thereby selectively laterally deflect end effector (40) at various angles relative to the longitudinal axis defined by shaft (30). In some examples the articulation control may be in the form of a rotary dial. In other examples, the articulation control may take numerous other forms. By way of example only, some merely illustrative forms that the articulation control and other components of handpiece (20) may take are disclosed in U.S. Pub. No. 2012/0078243, now U.S. Pat. No. 9,877,720, issued Jan. 30, 2018, the disclosure of which is incorporated by reference herein; in U.S. Pub. No. 2012/0078244, entitled "Control Features for Articulating Surgical Device," published Mar. 29, 2012, the disclosure of which is incorporated by reference herein; and in U.S. Pub. No. 2013/0023868, now U.S. Pat. No. 9,545,253, issued Jan. 17, 2017, the disclosure of which is incorporated by reference herein. Still other suitable forms that the articulation control may take will be apparent to those of ordinary skill in the art in view of the teachings herein. It should also be understood that some versions of instrument (10) may simply lack the articulation control.

B. Exemplary End Effector

End effector (40) of the present example comprises a first jaw (42) and a second jaw (44). In the present example, first jaw (42) is substantially fixed relative to shaft (30); while second jaw (44) pivots relative to shaft (30), toward and away from first jaw (42). Use of the term "pivot" should not be read as necessarily requiring pivotal movement about a fixed axis. In some versions, second jaw (44) pivots about an axis that is defined by a pin (or similar feature) that slides along an elongate slot or channel as second jaw (44) moves toward first jaw (42). In such versions, the pivot axis translates along the path defined by the slot or channel while second jaw (44) simultaneously pivots about that axis. It should be understood that such sliding/translating pivotal movement is encompassed within terms such as "pivot," "pivots," "pivotal," "pivotable," "pivoting," and the like. Of course, some versions may provide pivotal movement of second jaw (44) about an axis that remains fixed and does not translate within a slot or channel, etc.

In some versions, actuators such as rods or cables, etc., may extend through sheath (32) and be joined with second jaw (44) at a pivotal coupling (43), such that longitudinal movement of the actuator rods/cables/etc. through shaft (30) provides pivoting of second jaw (44) relative to shaft (30) and relative to first jaw (42). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
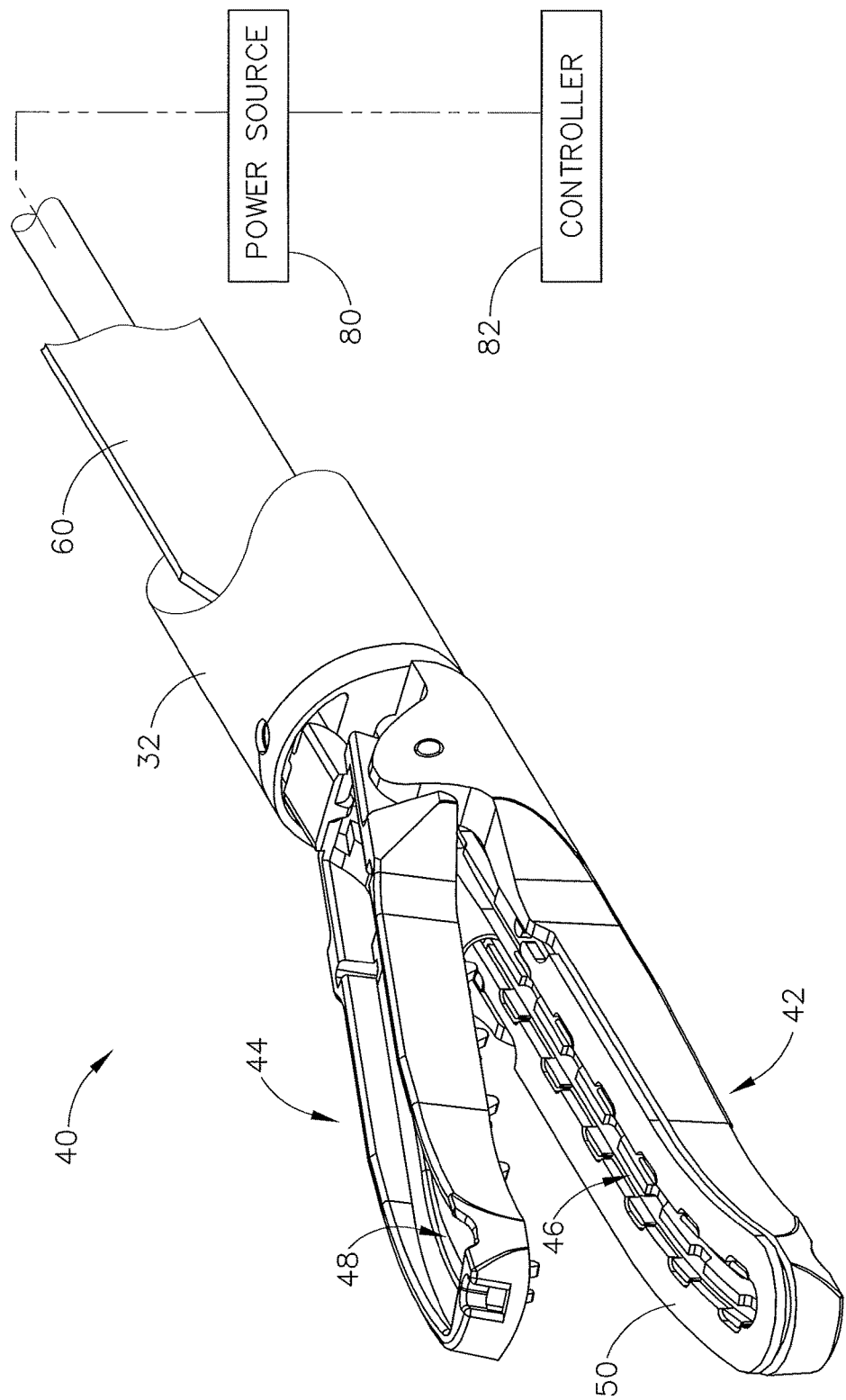
FIG. 2 depicts a perspective view of the end effector of the instrument of FIG. 1, in an open configuration.
Figure 3:
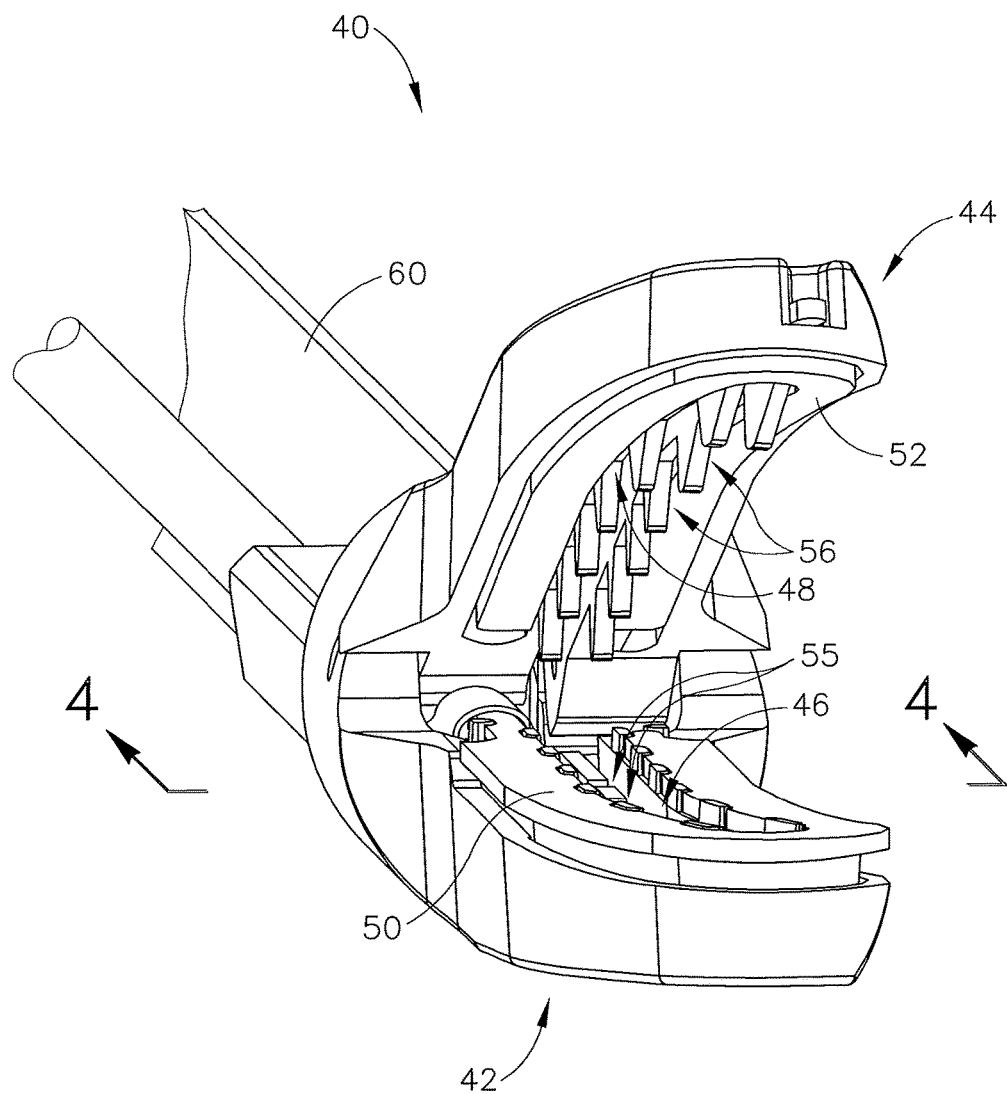
FIG. 3 depicts another perspective view of the end effector of the instrument of FIG. 1, in an open configuration.
Figure 4:
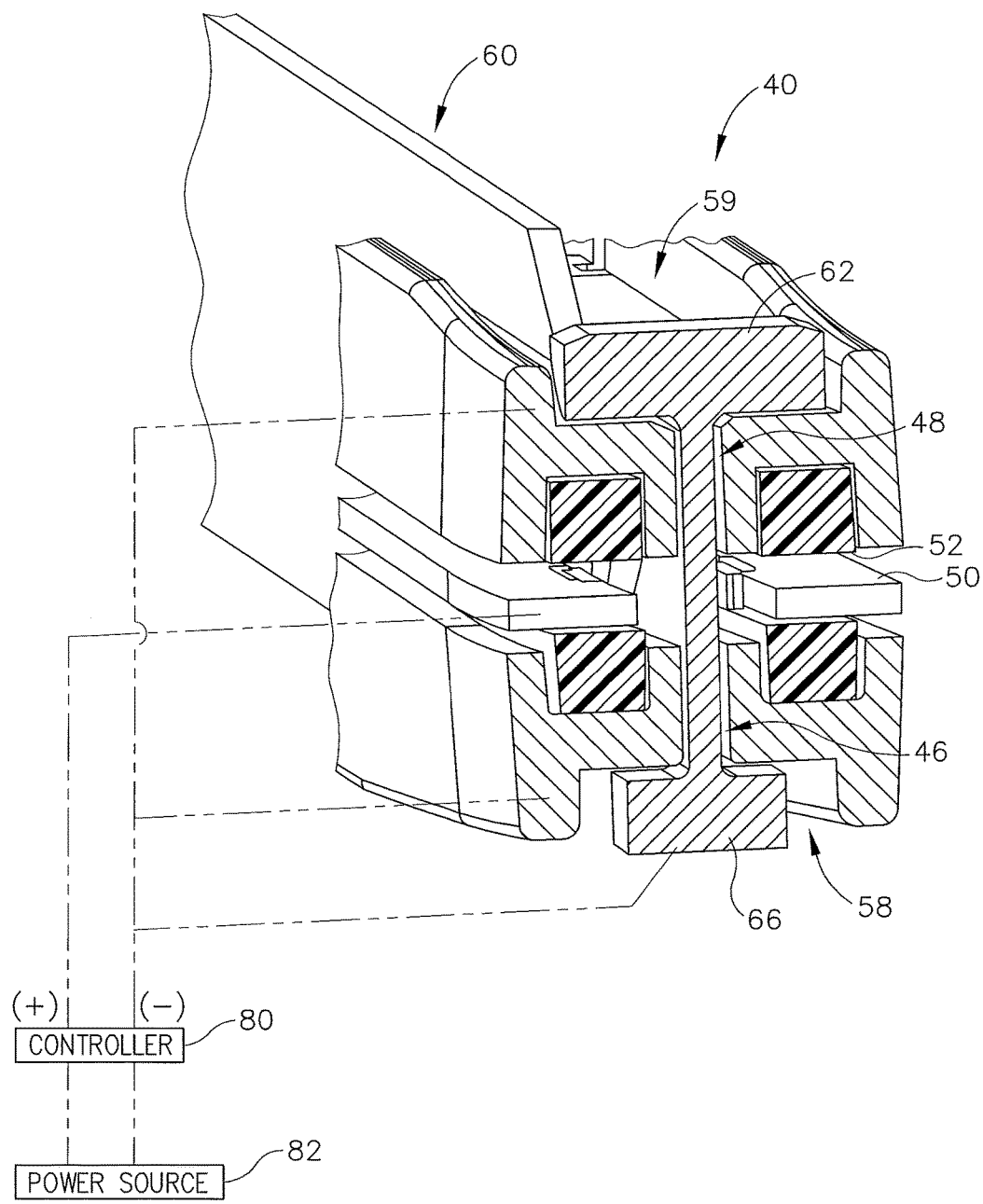
FIG. 4 depicts a cross-sectional end view of the end effector of FIG. 2, taken along line 4-4 of FIG. 3, in a closed configuration and with the firing beam in a distal position.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode (50); while the underside of second jaw (44) presents a second electrode (52). Electrodes (50, 52) are in communication with an electrical source (80) via one or more conductors (not shown) that extend along the length of shaft (30). These conductors are coupled with electrical source (80) and a controller (82) via a cable (84), which extends proximally from handpiece (20). Electrical source (80) is operable to deliver RF energy to first electrode (50) at an active polarity while second electrode (52) serves as a reference/return passive electrode, such that RF current flows between electrodes (50, 52) and thereby through tissue captured between jaws (42, 44). There are instances where the active signal crosses zero potential that the reference is at the same potential so there is no current flow. In some versions, firing beam (60) serves as an electrical conductor that cooperates with electrodes (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrodes (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrodes (50, 52) may be provided in a variety of alternative locations, configurations, and relationships.

By way of example only, power source (80) and/or controller (82) may be configured in accordance with at least some of the teachings of U.S. Provisional Pat. App. No. 61/550,768, entitled "Medical Instrument," filed Oct. 24, 2011, the disclosure of which is incorporated by reference herein; U.S. Pub. No. 2011/0082486, entitled "Devices and Techniques for Cutting and Coagulating Tissue," published Apr. 7, 2011, now U.S. Pat. No. 9,089,360, issued Jul. 28, 2015, the disclosure of which is incorporated by reference herein; U.S. Pub. No. 2011/0087212, entitled "Surgical Generator for Ultrasonic and Electrosurgical Devices," published Apr. 14, 2011, now U.S. Pat. No. 8,986,302 issued Mar. 24, 2015, the disclosure of which is incorporated by reference herein; U.S. Pub. No. 2011/0087213, entitled "Surgical Generator for Ultrasonic and Electrosurgical Devices," published Apr. 14, 2011, now U.S. Pat. No. 8,951,248, issued Feb. 10, 2015, the disclosure of which is incorporated by reference herein; U.S. Pub. No. 2011/0087214, entitled "Surgical Generator for Ultrasonic and Electrosurgical Devices," published Apr. 14, 2011, now U.S. Pat. No. 9,039,695, issued May 26, 2015, the disclosure of which is incorporated by reference herein; U.S. Pub. No. 2011/0087215, entitled "Surgical Generator for Ultrasonic and Electrosurgical Devices," published Apr. 14, 2011, now U.S. Pat. No. 9,050,093, issued Jun. 9, 2015, the disclosure of which is incorporated by reference herein; U.S. Pub. No. 2011/0087216, entitled "Surgical Generator for Ultrasonic and Electrosurgical Devices," published Apr. 14, 2011, now U.S. Pat. No. 8,956,349, issued Feb. 17, 2015, the disclosure of which is incorporated by reference herein; and/or U.S.

Pub. No. 2011/0087217, entitled "Surgical Generator for Ultrasonic and Electrosurgical Devices," published Apr. 14, 2011, now U.S. Pat. No. 9,060,776, issued Jun. 23, 2015, the disclosure of which is incorporated by reference herein. Other suitable configurations for power source (80) and controller (82) will be apparent to those of ordinary skill in the art in view of the teachings herein.

As best seen in FIG. 4, the lower side of first jaw (42) includes a longitudinally extending recess (58) adjacent to slot (46); while the upper side of second jaw (44) includes a longitudinally extending recess (59) adjacent to slot (48). FIGS. 2 and 3 show the upper side of first jaw (42) including a plurality of teeth recesses (55). Correspondingly, the lower side of second jaw (44) includes complementary teeth serrations (56) that nest within recesses (55), to enhance gripping of tissue captured between jaws (42, 44) without necessarily tearing the tissue. In other words, it should be understood that serrations (56) may be generally blunt or otherwise atraumatic. Although FIG. 3 shows first jaw having recesses (55) and second jaw (44) serrations (56) as, it should be understood that recesses (55) and serrations (56) may take any other suitable form or may be simply omitted altogether. It should also be understood that serrations (56) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44). In some versions, serrations (56) are electrically conductive.

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrodes (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (not shown) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrodes (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, the PTC thermistor bodies at end effector (40) may automatically reduce the energy delivery at electrodes (50, 52) as the temperature of the tissue and/or end effector (40) increases, thereby reducing the likelihood of overheating. In some such versions, a PTC thermistor element is in series with power source (80) and electrode (50, 52); and the PTC thermistor provides an increased impedance (reducing flow of current) in response to temperatures exceeding a threshold. Furthermore, it should be understood that electrodes (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

Figure 5:
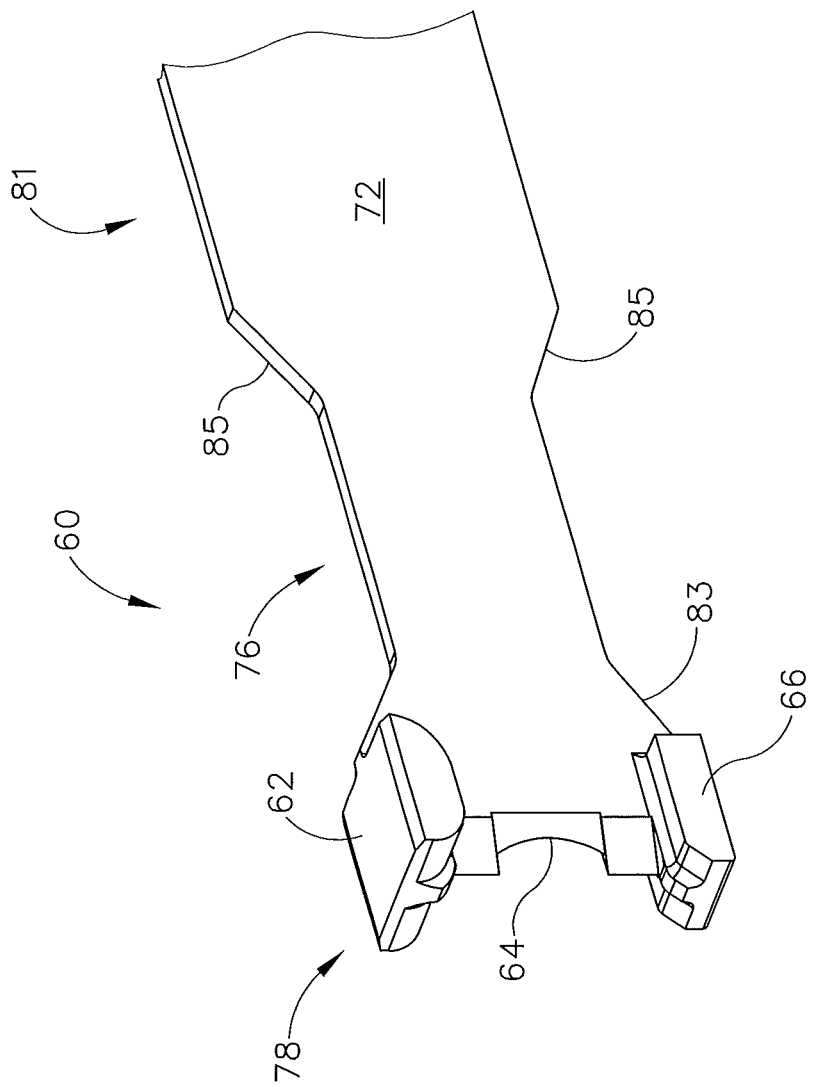
FIG. 5 depicts a partial perspective view of the distal end of the firing beam of the end effector of FIG. 2.
Figure 6:
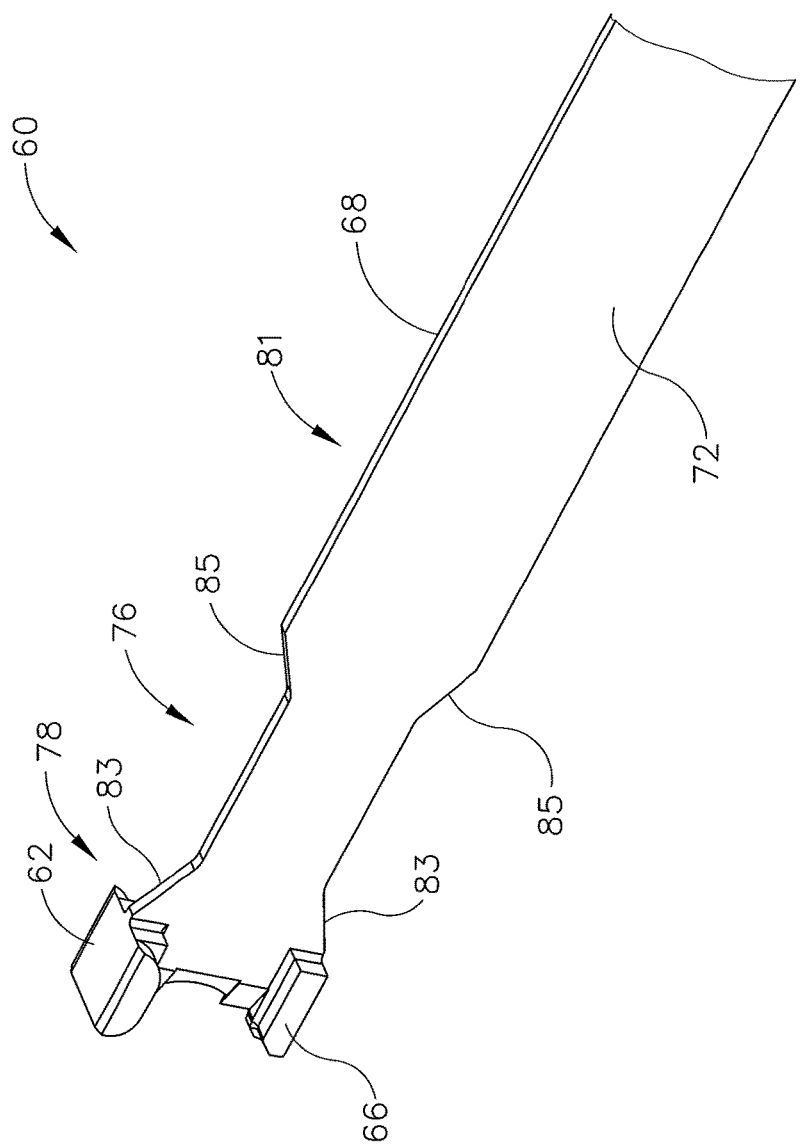
FIG. 6 depicts another partial perspective view of the distal end of the firing beam of FIG. 5.

As also seen in FIGS. 2-8, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. In some versions, a proximal end of firing beam (60) is secured to a firing tube or other structure within shaft (30); and the firing tube or other structure extends through the remainder of shaft (30) to handpiece (20) where it is driven by movement of trigger (24). As best seen in FIG. 5, firing beam (60) includes a sharp distal blade (64), an upper flange (62), and a lower flange (66). As shown best in FIGS. 6-8, firing beam (60) of the present example includes an upper wall (68), a lower wall (70), a first side wall (72), and a second, opposing side wall (74). At least a portion of firing beam (60) can be described by a length (l), width (w), and height (h). Firing beam (60) includes an intermediate portion (76) between a distal portion (78) and proximal portion (81). As shown, the distance between the upper and lower walls (68, 70) decreases from the distal portion (78) to the intermediate portion (76), and again increases from the intermediate portion (76) to the proximal portion (81). In other words, the intermediate portion (76) includes a section where a height dimension of the intermediate portion (76) is less than a height dimension of both the distal portion (78) and the proximal portion (81). As shown, firing beam (60) includes a distal tapered portion (83) and a proximal tapered portion (85) on each of the upper and lower walls (68, 70).

As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade (64) will readily sever tissue that is captured between jaws (42, 44). Distal blade (64) is also electrically grounded in the present example, providing a return path for RF energy as described elsewhere herein. In some other versions, distal blade (64) serves as an active electrode.

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze trigger (24) to actuate firing beam (60) through a full firing stroke. In other words, in some such versions, firing beam (60) may have already overcome an initial resistance required to substantially close jaws (42, 44) on tissue before encountering resistance from severing the tissue captured between jaws (42, 44). Of course, any other suitable staging may be provided.

In the present example, flange (62) is configured to cam against a ramp feature at the proximal end of jaw (44) to open jaw (44) when firing beam (60) is retracted to a proximal position and to hold jaw (44) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

In some variations, firing beam (60) is modified such that flanges (62, 66) are replaced with pins that extend transversely from the modified firing beam. In other words, one or more upper pins could bear against recess (59) of jaw (44), and one or more lower pins could bear against recess (58) of jaw (42), as the modified firing beam is advanced distally through slots (46, 48). In some such versions, one or more of the pins may be configured to rotate about axes that extend transversely from the modified firing beam, such that the pins roll along recesses (58, 59) as the modified firing beam translates longitudinally through slots (46, 48). The pins may thus provide reduced friction with jaws (42, 44), thereby reducing the force required to translate the modified firing beam. In addition or in the alternative, at least one of the pins may be slidably disposed in a corresponding elongate slot formed through the modified firing beam, such that the pin may translate along a plane defined by the modified firing beam. By way of example only, a modified firing beam may be configured in accordance with at least some of the teachings of U.S. Pub. No. 2012/0083783, now U.S. Pat. No. 8,888,809, issued Nov. 18, 2014, the disclosure of which is incorporated by reference herein. Other suitable ways in which firing beam (60) may be varied will be apparent to those of ordinary skill in the art in view of the teachings herein.

D. Exemplary Operation

In an exemplary use, end effector (40) is inserted into a patient via a trocar. Articulation section (36) is substantially straight when end effector (40) and part of shaft (30) are inserted through the trocar. The articulation control, if equipped, may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (44) toward jaw (42) when firing beam (60) is actuated distally by squeezing trigger (24) toward pistol grip (22). Jaws (42, 44) may be substantially clamping tissue before trigger (24) has swept through a full range of motion toward pistol grip (22), such that trigger (24) may continue pivoting toward pistol grip (22) through a subsequent range of motion after jaws (42, 44) have substantially clamped on the tissue.

With tissue layers captured between jaws (42, 44) firing beam (60) continues to advance distally by the user squeezing trigger (24) further toward pistol grip (22). As firing beam (60) continues to advance distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, help keep jaws (42, 44) in a closed and tightly clamping position. In particular, flanges (62, 66) help maintain a significantly compressive force between jaws (42, 44). With severed tissue layer portions being compressed between jaws (42, 44), bipolar RF energy is applied to the tissue through electrodes (50, 52) by the user depressing activation button (26). Thus, a bipolar RF current flows through the compressed regions of severed tissue layer portions. The bipolar RF energy delivered by power source (80) ultimately thermally welds the tissue layer portions on one side of firing beam (60) together and the tissue layer portions on the other side of firing beam (60) together.

In certain circumstances, the heat generated by activated electrodes (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrodes (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrodes (50, 52). Other suitable ways in which instrument (10) may be operable and operated will be apparent to those of ordinary skill in the art in view of the teachings herein.

II. Exemplary Tissue Removal Features

Figure 9:
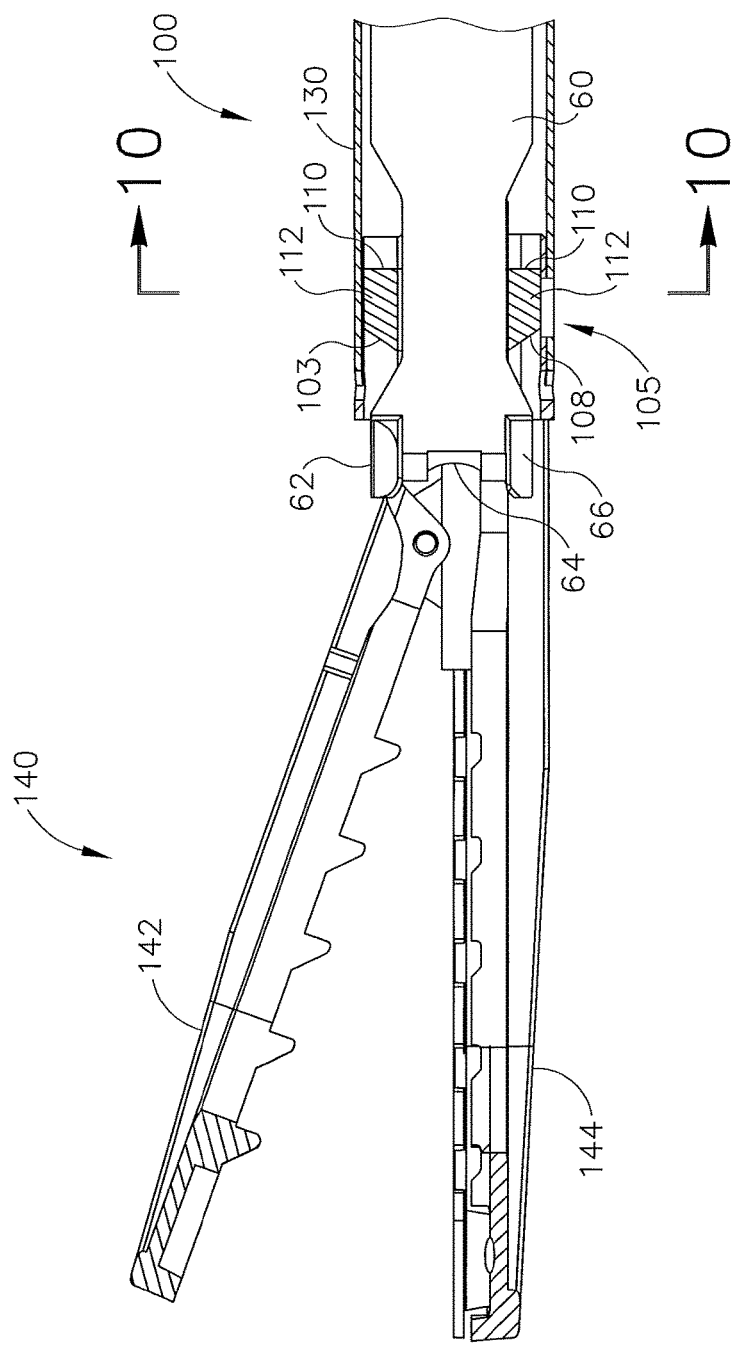
FIG. 9 depicts a cross-sectional side view of an exemplary alternative shaft assembly and end effector that may be incorporated into the instrument of FIG. 1, taken along line 9-9 of FIG. 11, with the firing beam of FIG. 6 incorporated therein, showing a set of upper and lower tissue removal features.
Figure 10:
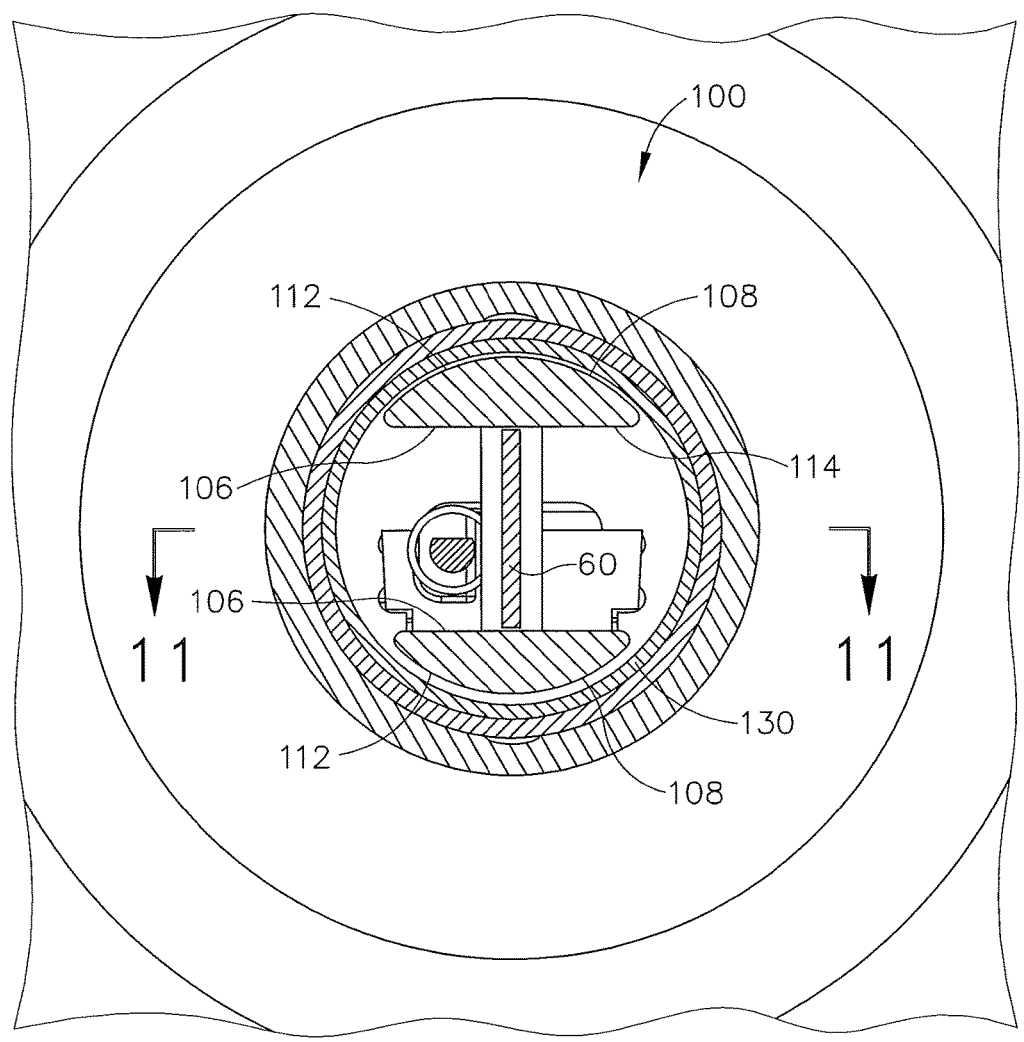
FIG. 10 depicts a cross-sectional end view of the shaft assembly of FIG. 9, taken along line 10-10 of FIG. 9.
Figure 11:
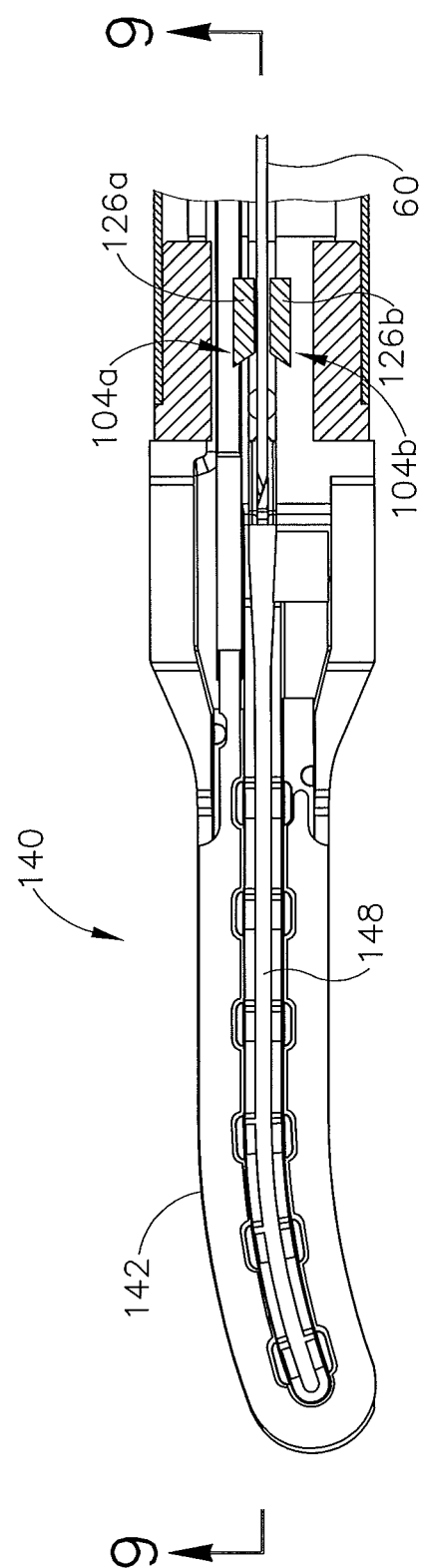
FIG. 11 depicts a cross-sectional top view of the shaft assembly of FIG. 9, taken along line 11-11 of FIG. 10, showing a set of side tissue removal features.
Figure 12:
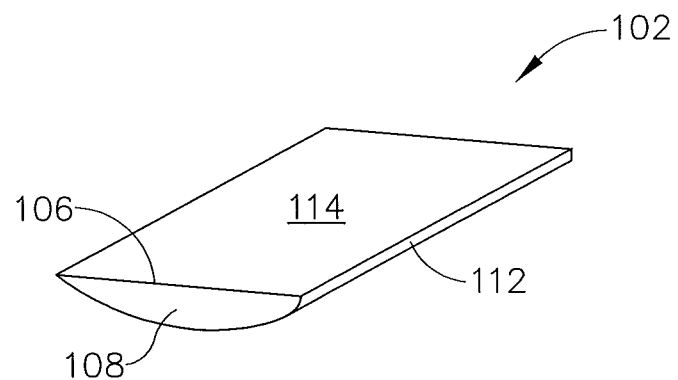
FIG. 12 depicts a perspective view of one of the tissue removal features of FIG. 9.
Figure 13:
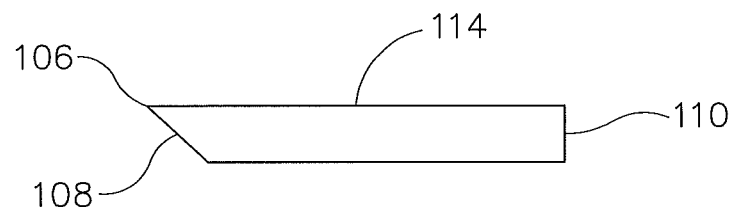
FIG. 13 depicts a side elevational view of one of the tissue removal features of FIG. 9.
Figure 14:
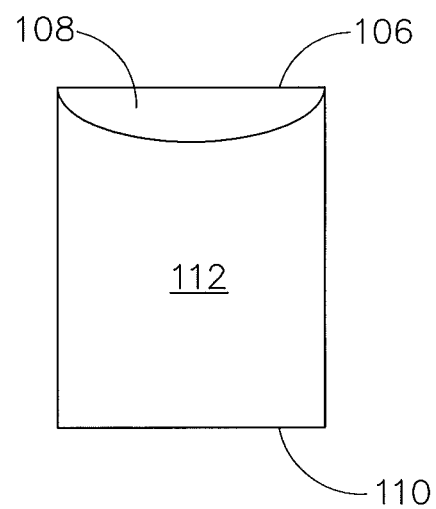
FIG. 14 depicts a plan view of one of the tissue removal features of FIG. 9.
Figure 15:
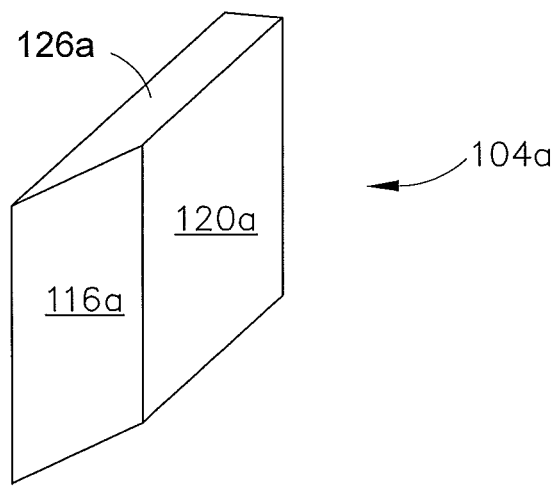
FIG. 15 depicts a perspective view of a first side tissue removal feature of FIG. 11.
Figure 16:
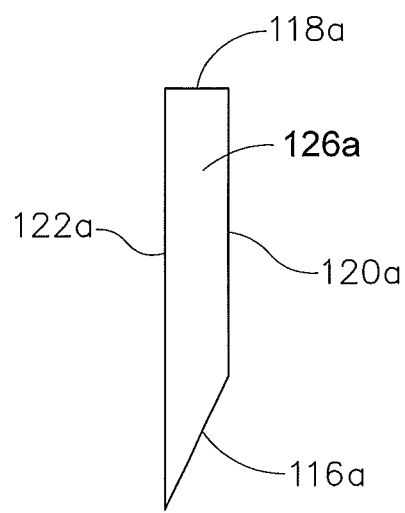
FIG. 16 depicts a top view of the first side tissue removal feature of FIG. 11.
Figure 17:
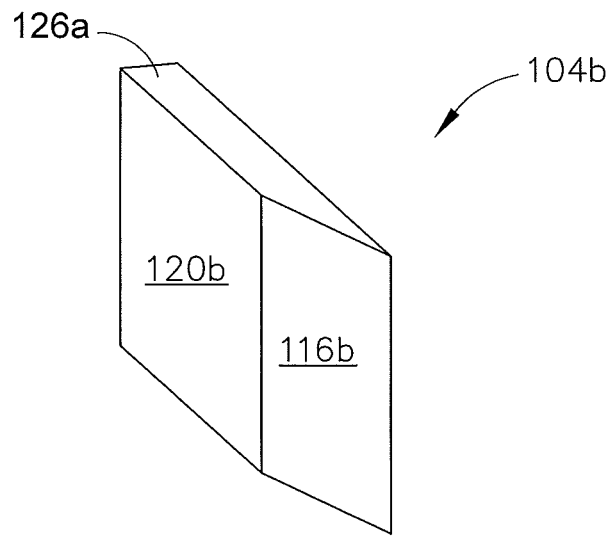
FIG. 17 depicts a perspective view of a second side tissue removal feature of FIG. 11.
Figure 18:
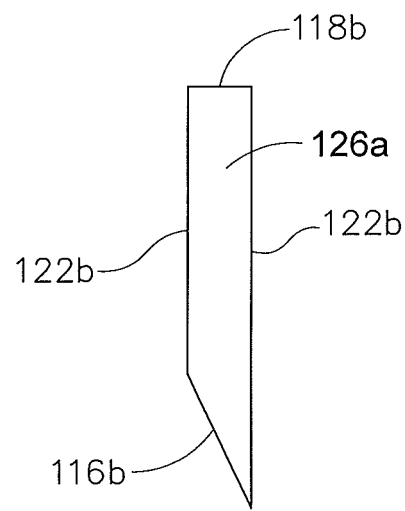
FIG. 18 depicts a top view of a second side tissue removal feature of FIG. 11.

After operating instrument (10) to clamp, sever, and weld tissue as described above, some of the affected tissue may tend to eventually stick to firing beam (60). In addition or in the alternative, blood may tend to eventually coagulate on firing beam (160), other fluids may tend to eventually build up on firing beam (60), and/or other debris may tend to eventually build up on firing beam (60). In some instances, such tissue, coagulated blood, fluids, and/or other debris that becomes stuck on firing beam (60) may eventually collect in the end effector (140), such as within slots (46, 48) of jaws (42, 44) (or slot (148) of jaw (142) shown in FIG. 9). This build-up may increase the force required to reciprocate firing beam (60) within end effector (40), and may therefore makes it more difficult to advance firing beam (60) along slots (42, 44) during each subsequent firing. FIGS. 9-11 show an exemplary alternative shaft assembly (100) including features that provide the removal of debris from firing beam (60) and thus prevent debris from building up on the firing beam (60).

It should be understood that shaft assembly (100) of the present example may be readily incorporated into instrument (10) described above. It should also be understood that, in many respects, shaft assembly (100) functions substantially similar to shaft (30) described above. Thus, a version of instrument (10) that is equipped with shaft assembly (100) of the present example may be configured and operable similar instrument (10) described above, except for the differences discussed below.

An end effector (140) is located at the distal end of shaft assembly (100). End effector (140) of the present example functions substantially similar to end effector (40) described above except for the differences discussed below. In particular, end effector (140) may be used to capture tissue, apply RF energy to the captured tissue to seal the captured tissue, and sever the captured tissue after or during the sealing of the tissue in a substantially similar manner as described above. Jaws (142, 144) may be actuated by firing beam (60) in a substantially similar manner to that described above with respect to jaws (42, 44) and firing beam (60). Alternatively, by way of example only, one or more cables, rods, beams, or other features may extend through shaft (130) to selectively actuate jaws (142, 144) independently of firing beam (60). Such jaw (142, 144) actuation features may be separately controlled by a dedicated feature of a handpiece (e.g., similar to handpiece (20)). Alternatively, such jaw actuation features may be controlled by a trigger (e.g., similar to trigger (24)) in addition to having trigger (124) control firing beam (60). It should also be understood that firing beam (60) may be resiliently biased to a proximal position, such that firing beam (60) retracts proximally when a user relaxes their grip on trigger.

Shaft assembly (100) of the present example includes a set of upper and lower tissue removal features (102) (FIGS. 9-10 and 12-14) and a set of side tissue removal features (104a, 104b) (FIGS. 11 and 15-18). As described herein, tissue removal features (102, 104a, 104b) may be referred to as "scrapers" due to their ability to scrape debris from firing beam (60). In particular, the upper and lower tissue scrapers (102) are positioned and configured to scrape debris from top and bottom walls (68, 70) of firing beam (60), respectively. Similarly, the side tissue scrapers (104a, 104b) are configured and positioned to scrape debris from respective side walls (72, 74) of firing beam (60). As shown in FIG. 9, outer sheath (130) of shaft assembly includes a lateral opening (105) through which debris may fall after being scraped from firing beam (60) by tissue scrapers (102, 104a, 104b). It should be understood that lateral opening (105) may have a variety of configurations, including but not limited to a round hole, an elongate opening, etc. Moreover, more than one lateral opening (105) may be provided. It should also be understood that a pressurized fluid may be introduced through lateral opening (105) to assist in flushing the debris from shaft assembly (100).

As best shown in FIGS. 9-10 and 12-14, upper and lower tissue scrapers (102) of the present example each include an angled front face (108), a flat rear face (110), a curvilinear face (112) between front face (108) and rear face (110), and a second flat face (114) also extending between front face (108) and rear face (110). Front face (108) and second flat face (114) further define a scraping edge (106). Thus, front face (108) and scraping edge (106) define a wedge shaped portion that acts as a ramp to remove debris from firing beam (60). Upper and lower scrapers (102) are fixedly positioned in the shaft (130) such that second flat face (114) of each scraper (102) faces and is positioned parallel with respect to a longitudinal axis along which shaft assembly (100) extends. Moreover, scrapers (102) are positioned such that front faces (108) extend away from the longitudinal axis at an acute angle relative to the longitudinal axis and in the proximal direction. In the example shown, the acute angle is approximately 45 degrees. In some other versions, the angle is between approximately 10 degrees and approximately 80 degrees, or more particularly between approximately 20 degrees and approximately 70 degrees, or more particularly between approximately 30 degrees and approximately 60 degrees, or more particularly between approximately 40 degrees and approximately 50 degrees. As shown, second flat face (114) of each scraper (102) is positioned to bear against upper and lower walls (68, 70) respectively, of firing beam (60). It will be understood that in other examples, upper and lower scrapers (102) may include different shapes or sizes relative to shaft (130) and other components of instrument (100). In those and other examples upper and lower scrapers (102) need not necessarily be identically shaped, but rather may be shaped differently than each other.

Side tissue scrapers (104a, 104b) of the present example are shown in FIG. 11 as being configured and positioned to bear against and scrape debris from respective side walls (72, 74) of firing beam (60). First side tissue scraper (104a) of the present example includes an angled front face (116a), a rear face (118a), and opposing side faces (120a, 122a) extending between the front and rear faces (116a, 118a), and opposing upper and lower faces (126a, 128a). As shown, second side tissue scraper (104b) is essentially a mirror image of first side tissue scraper (104a). In that regard, second side tissue scraper (104b) of the present example includes an angled front face (116b), a rear face (118b), and opposing side faces (120b, 122b) extending between the front and rear faces (116b, 118b), and opposing upper and lower faces (126b, 128b). As shown, side tissue scrapers (104a, 104b) are positioned within shaft such that side faces (120a, 120b) bear against a respective side wall (68, 70) of firing beam (60). Moreover, side tissue scrapers (104a, 104b) are positioned such that angled front faces (116a, 116b) extend away from the longitudinal axis at an acute angle in the distal direction. In the example shown, the acute angle is approximately 45 degrees. In some other versions, the angle is between approximately 10 degrees and approximately 80 degrees, or more particularly between approximately 20 degrees and approximately 70 degrees, or more particularly between approximately 30 degrees and approximately 60 degrees, or more particularly between approximately 40 degrees and approximately 50 degrees. As shown, angled front faces (116a, 116b) act as a ramp to remove tissue or other material from firing beam (60). It will be understood that in other examples, side tissue scrapers (104a, 104b) may include different shapes or sizes relative to shaft (130) and other components of instrument (100). In those and other examples side tissue scrapers (104a, 104b) need not necessarily be identically shaped as shown, but rather may be shaped differently than each other.

Scrapers (102, 104a, 104b) in the example shown are elastically deformable in order to allow passage of firing beam (60) between proximal and distal positions. As best shown in FIG. 9, upper and lower scrapers (102) are positioned adjacent to (or are bearing against) upper and lower walls (68, 70) of firing beam (60) along intermediate portion of firing beam (60), while the firing beam (60) is in the proximal position. As firing beam (60) advances distally, upper and lower scrapers (102) are borne against by respective proximal tapered portions (85) of firing beam (60) and eventually proximal portions (81) of upper and lower walls (68, 70) of firing beam (60). Therefore, at least a central portion of upper and lower scrapers (102) are elastically deformed as firing beam (60) advances. Similarly, at least a portion of side scrapers (104a, 104b) may be positioned coincident with intermediate portion (76) of firing beam (60) when firing beam (60) is in the proximal position. Thus, at least a portion of side scrapers (104a, 104b) need not necessarily be bearing at against a respective side wall (72, 74) of firing beam (60) when firing beam (60) is in the proximal position. As firing beam (60) is advanced distally, however, side scrapers (104a, 104b) eventually bear against respective side walls (72, 74) of firing beam (60), and are also elastically deformed as firing beam (60) advances distally. Of course, as firing beam (60) returns to its proximal position, scrapers (102, 104a, 104b) may return to their undeformed states. Alternatively, scrapers (102, 104a, 104b) may also be deformed when firing beam (60) is in the proximal position, albeit less deformed than when firing beam (60) is in the distal position.

In order to reduce the frictional force between scrapers (102, 104a, 104b) and firing beam (60), one or more scrapers (102, 104a, 104b) may include a lubricious material. For example, scrapers (102, 104a, 104b) may be made from a lubricious material or may be coated with a lubricious material, such as silicone. In addition or in the alternative, scrapers (102, 104a, 104b) may comprise a non-stick material such as polytetrafluoroethylene (PTFE). The lubricious material may also assist in releasing tissue from scrapers (102, 104a, 104b) after scrapers (102, 104a, 104b) have scraped tissue from firing beam (60). In addition or in the alternative, firing beam (60) may include a lubricious material. For example, firing beam (60) may be made from a lubricious material or may be coated with a lubricious material, such as silicone. In addition or in the alternative, firing beam (60) may comprise PTFE material. It will be understood that the positions of scrapers (102, 104a, 104b) is not limited to those positions shown in the figures. For example, rather than being disposed within sheath (130), all or some of scrapers (102, 104a, 104b) may be disposed in portions of the end effector (140). It will be further understood that there may be more or less of either scrapers (102) or scrapers (104a, 104b) than the number shown in the figures.

In operation, after using instrument (100) to clamp, sever, and weld tissue as described above, some of the affected tissue, coagulated blood, etc. may stick to firing beam (60). As the firing beam (60) retracts to its proximal position, the portion of the stuck debris on the top wall (68) of firing beam (60), if any, will reach upper scraper (102) and will initially contact corresponding scraping edge (106) and front face (106), and will be scraped from firing beam (60) and fall through lateral opening (105). Similarly, debris stuck on bottom wall (70) of firing beam (60), if any, will reach corresponding lower scraper (104) and will initially contact corresponding scraping edge (106) and front face (106), and will be scraped from firing beam (60) and fall through lateral opening (105). Debris stuck on side walls (72, 74) of firing beam (60), if any is present, will reach a corresponding side scraper (104a, 104b) and will initially contact a respective angled front face (116a, 116b), and will be scraped from firing beam (60) and fall through opening. Thus, because debris is scraped from firing beam (60) each time firing beam (60) is returned to a proximal position after being advanced distally, the amount of debris collecting in slots or other part of shaft assembly (100) is diminished and subsequent firings of firing beam (60) are not significantly impeded.

III. Miscellaneous

It should be understood that any of the versions of electrosurgical instrument (10) described herein may include various other features in addition to or in lieu of those described above. By way of example only, any of the devices herein may also include one or more of the various features disclosed in any of the various references that are incorporated by reference herein.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410, 603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

In versions where the teachings herein are applied to a surgical stapling instrument, it should be understood that the teachings herein may be combined with the teachings of one or more of the following, the disclosures of all of which are incorporated by reference herein: U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010, now U.S. Pat. No. 8,408,439, issued Apr. 2, 2013; and U.S. Pub. No. 2012/0239012, entitled "Motor-Driven Surgical Cutting Instrument with Electric Actuator Directional Control Assembly," published Sep. 20, 2012, now U.S. Pat. No. 8,453,914, issued Jun. 4, 2013. Other suitable ways in which the teachings herein may be applied to a surgical stapling instrument will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874, entitled "Tissue Pad for Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An apparatus for operating on tissue, the apparatus comprising:
   (a) a body;
   (b) an elongate shaft, wherein the elongate shaft extends distally from the body, and wherein the elongate shaft comprises at least one lateral opening proximal to a distal end of the elongate shaft; and
   (c) an end effector, wherein the end effector is disposed at the distal end of the elongate shaft, and wherein the end effector comprises:
      (i) a first jaw,
      (ii) a second jaw, wherein the first jaw is selectively pivotable toward and away from the second jaw to capture a tissue, and
      (iii) a firing beam configured to advance relative to the first and second jaws to sever the captured tissue and retract relative to the first and second jaws after the captured tissue has been severed;
   (d) a debris removal element in communication with the firing beam, wherein the debris removal element is disposed within the elongate shaft proximal to the distal end such that the debris removal element is contained within the elongate shaft adjacent to the at least one lateral opening, wherein the debris removal element is configured to engage at least a portion of the firing beam within the elongate shaft and remove at least a portion of debris from the firing beam at least during retraction of the firing beam relative to the first and second jaws, wherein the at least one lateral opening is configured to receive the debris removed by the debris removal element within the elongate shaft and thereby transfer the removed debris out of the elongate shaft.

2. The apparatus of claim 1, wherein the debris removal element is disposed on the elongate shaft.

3. The apparatus of claim 1, wherein the debris removal element is configured to elastically deform as the debris removal element engages the firing beam.

4. The apparatus of claim 1, wherein the debris removal element comprises a lubricious coating.

5. The apparatus of claim 1, wherein the shaft extends along a longitudinal axis, wherein the debris removal element includes a scraping edge oriented perpendicular to the longitudinal axis.

6. The apparatus of claim 5, wherein the firing beam includes a pair of opposing side walls, wherein the scraping edge is oriented perpendicular relative to the opposing side walls.

7. The apparatus of claim 5, wherein the firing beam includes a pair of opposing side walls, wherein the scraping edge is oriented parallel relative to the opposing side walls.

8. The apparatus of claim 1, wherein the firing beam includes a distal portion, a proximal portion, and an intermediate portion therebetween, wherein the intermediate portion includes a section that includes a height dimension that is less than a height dimension of at least the proximal portion.

9. The apparatus of claim 8, wherein the firing beam further comprises a tapered portion between the intermediate portion and either one of, or both of, the proximal portion and the distal portion.

10. The apparatus of claim 8, wherein the debris removal element is configured to elastically deform when the proximal portion of the firing beam bears against the debris removal element.

11. The apparatus of claim 8, wherein at least a portion of the debris removal element is coincident with the intermediate portion when the firing beam is in a retracted position.

12. The apparatus of claim 8, wherein the intermediate portion is spaced from the debris removal element when the firing beam is in an advanced position.

13. The apparatus of claim 1, wherein the debris removal element further comprises a pair of opposing scraping elements, wherein each of the scraping elements is configured to engage an opposing side of the firing beam.

14. The apparatus of claim 1, wherein at least a portion of the debris removal element is coincident with the at least one lateral opening.

15. An apparatus for operating on tissue, the apparatus comprising:
(a) a body;
(b) an elongate shaft, wherein the elongate shaft extends distally from the body, and wherein the elongate shaft comprises a distal end and an inner wall; and
(c) an end effector, wherein the end effector is disposed at the distal end of the elongate shaft, and wherein the end effector comprises:
(i) a first jaw,
(ii) a second jaw, wherein the first jaw is selectively pivotable toward and away from the second jaw to capture a tissue, and
(iii) a translating element configured to advance relative to the first and second jaws to sever the captured tissue and to retract relative to the first and second jaws after the captured tissue has been severed;
(d) an elastically deformable member disposed between the inner wall of the elongate shaft and the translating element such that the elastically deformable member is located inside the elongate shaft, wherein the elastically deformable member is configured to deform as the translating element advances, wherein the elastically deformable member is configured and positioned to maintain contact with the translating element as the translating element is advanced and retracted through a full range of longitudinal motion from a proximal-most position to a distal-most position such that the elastically deformable member is configured to scrape at least a portion of the translating element, wherein at least one lateral opening disposed proximal to the distal end of the elongated shaft is configured to receive debris removed by the elastically deformable member within the elongate shaft, and
wherein the elastically deformable member is disposed within the elongate shaft proximal to the distal end such that the elastically deformable member is contained within the elongate shaft adjacent to the at least one lateral opening.

16. The apparatus of claim 15, wherein the elastically deformable member comprises a wedge shaped portion that is configured to act as a ramp to drive the debris away from the translating element.

17. The apparatus of claim 15, wherein the elastically deformable member comprises a lubricious material.

18. An apparatus for operating on tissue, the apparatus comprising:
(a) a body;
(b) an elongate shaft, wherein the elongate shaft extends distally from the body, and wherein the elongate shaft comprises a distal end and at least one lateral opening proximal to the distal end; and
(c) an end effector, wherein the end effector is disposed at the distal end of the elongate shaft, and wherein the end effector comprises:
(i) a first jaw,
(ii) a second jaw, wherein the first jaw is selectively pivotable toward and away from the second jaw to capture a tissue, and
(iii) a slidable blade configured to advance relative to the first and second jaws to sever the captured tissue and retract relative to the first and second jaws after the captured tissue has been severed;
(d) a scraper securely located within the distal end of the elongate shaft, wherein the scraper is in communication with the slidable blade and is configured to engage the slidable blade and thereby remove a portion of debris from the slidable blade during advancement or retraction of the slidable blade relative to the first and second jaws, wherein the at least one lateral opening is configured to receive the portion of debris removed by the scraper within the elongate shaft and thereby transfer the removed debris out of the elongate shaft.

19. The apparatus of claim 18, wherein the scraper is configured to deform within the elongate shaft as the slidable blade advances or retracts.

* * * * *